United States Patent [19]

Hall

[11] Patent Number: 4,627,935

[45] Date of Patent: Dec. 9, 1986

[54] 2-ISOPROPENYL-5-METHYLCYCLOPENTANEALKANOLS, ESTERS THEREOF AND ORGANOLEPTIC USES OF SAME

[75] Inventor: John B. Hall, Rumson, N.J.

[73] Assignee: International Flavors & Fragrances Inc., New York, N.Y.

[21] Appl. No.: 698,862

[22] Filed: Feb. 6, 1985

[51] Int. Cl.[4] .......................... C11B 9/00; A61K 7/46; C07C 35/06

[52] U.S. Cl. ................................ 252/522 R; 560/122; 568/838

[58] Field of Search ........................ 252/522; 568/838; 560/122

[56] References Cited

U.S. PATENT DOCUMENTS

| | | | |
|---|---|---|---|
| 4,069,258 | 1/1978 | Hoffmann et al. | 252/522 R |
| 4,318,831 | 3/1982 | Klein et al. | 252/522 R |

FOREIGN PATENT DOCUMENTS

| | | | |
|---|---|---|---|
| 52045 | 5/1975 | Japan | 568/838 |
| 604714 | 9/1978 | Sweden | 252/522 R |
| 572009 | 1/1976 | Switzerland | 568/838 |

*Primary Examiner*—Werren B. Lone

*Attorney, Agent, or Firm*—Arthur L. Liberman

[57] ABSTRACT

Described are the 2-isopropenyl-5-methylcyclopentanealkanols and esters thereof having the generic structure:

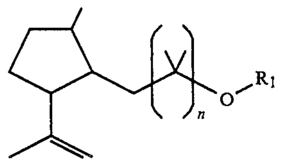

wherein $R_1$ represents hydrogen or $C_2$-$C_3$ acyl and wherein n represents 0 or 1 and uses thereof in augmenting or enhancing the aroma of consumable materials including perfume compositions, colognes and perfumed articles such as solid or liquid anionic, cationic, nonionic or zwitterionic detergents, perfumed polymers, cosmetic compositions, fabric softener compositions, fabric softener articles and hair preparations.

9 Claims, 8 Drawing Figures

FIG. I

NMR SPECTRUM FOR FRACTION II, EXAMPLE I.

NMR SPECTRUM FOR FRACTION 10, EXAMPLE II.

GLC PROFILE FOR FRACTION 5, EXAMPLE IV.

GLC PROFILE FOR FRACTION 4, EXAMPLE V.

NMR SPECTRUM FOR PEAK 41 OF EXAMPLE V, FRACTION 4.

NMR SPECTRUM FOR EXAMPLE IV, FRACTION 5.

2-ISOPROPENYL-5-METHYLCYCLOPENTANEALKANOLS, ESTERS THEREOF AND ORGANOLEPTIC USES OF SAME

BACKGROUND OF THE INVENTION

This invention is directed to 2-isopropenyl-5-methylcyclopentanealkanols and esters thereof defined according to the structure:

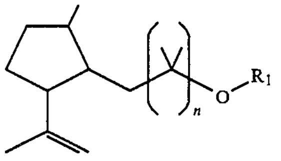

wherein $R_1$ represents hydrogen or $C_2$–$C_3$ acyl and n represents 0 or 1 and uses thereof in augmenting or enhancing the aroma of consumable materials.

Materials which can provide piney, woody, camphoraceous, minty, rosy, peppery, spicy, green, violet, ambery and vetiver aromas with eucalyptus, sweaty, carnation, green, ambery and cedarwood topnotes are well known and highly desirable in the art of perfumery. Many of the natural substances which provide such fragrances and contribute the desired nuances to perfumery compositions are high in cost, vary in quality from one batch to another and/or are generally subject to the usual variations of natural products.

The prior art contains a large number of teachings regarding the use of methyl-substituted cyclopentyl alkanol derivatives and esters thereof in augmenting or enhancing the aroma of perfumes. Thus, Givaudan, Swiss Pat. No. 604,714 issued on Sept. 15, 1978 discloses the compounds defined according to the generic structure:

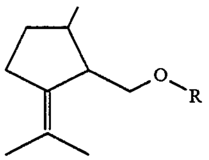

wherein R represents hydrogen or formyl for use in perfumery and discloses the compound having the structure:

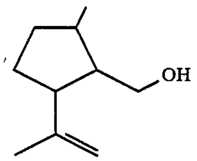

as an intermediate for producing such material. The perfume utilities of the compound having the structure:

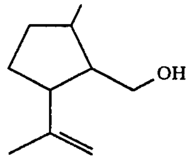

are not disclosed or inferred in Swiss Pat. No. 604,714.

The compound having the structure:

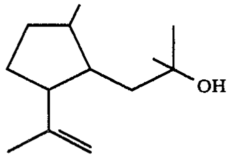

is disclosed by Edwards, et al "Selectivity in the Addition of Organic Radicals to the Alkene Bond, J.C.S. Chem. Comm. 1978, 438 [Abstracted in Chem. Abstracts, Volume 90, No. 21897w].

Nothing in the prior art, however, discloses the genus having the structure:

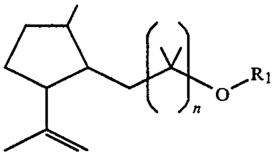

wherein $R_1$ represents hydrogen or $C_2$–$C_3$ acyl and n represents 0 or 1 for its organoleptic properties for use in perfumery and nothing in the prior art discloses or infers the genus having the structure:

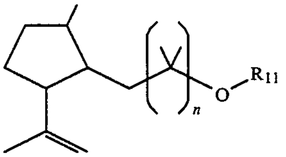

wherein $R_{11}$ represents $C_2$ or $C_3$ acyl and n represents 0 or 1.

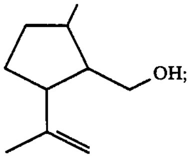

more specifically, approximately 70% of the compound having the structure:

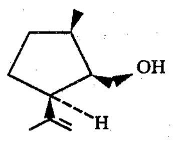

and about 15% of the compound having the structure:

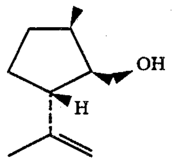

(Conditions: Field strength: 100 MHz; Solvent: $CFCl_3$).

Figure 2:
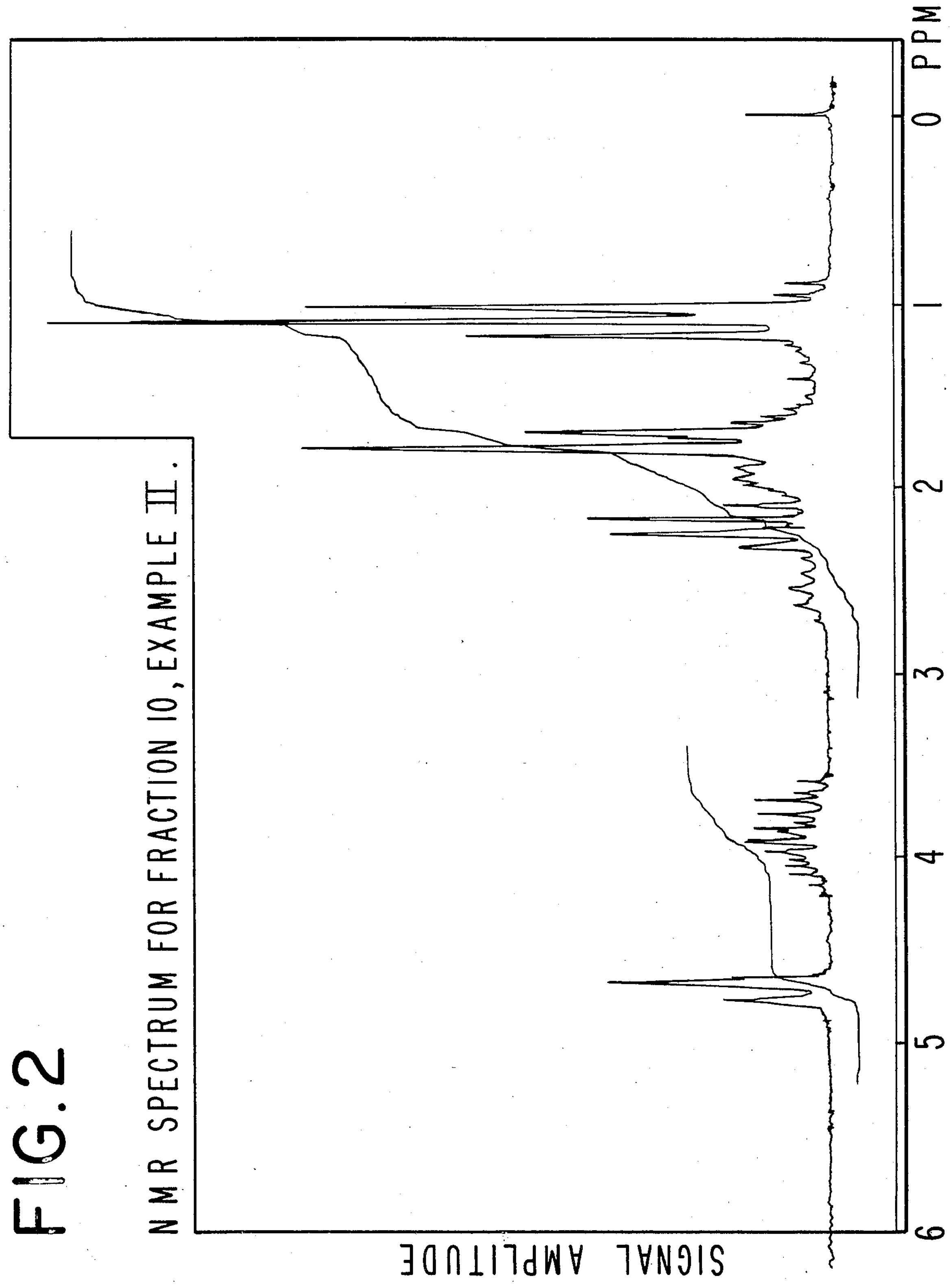

FIG. 2 is the NMR spectrum for Fraction 10 of the distillation of the reaction product of Example II containing the compound having the structure:

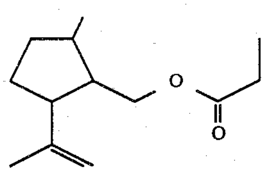

(Conditions: Field strength: 100 MHz; Solvent: $CFCl_3$).

Figure 3:
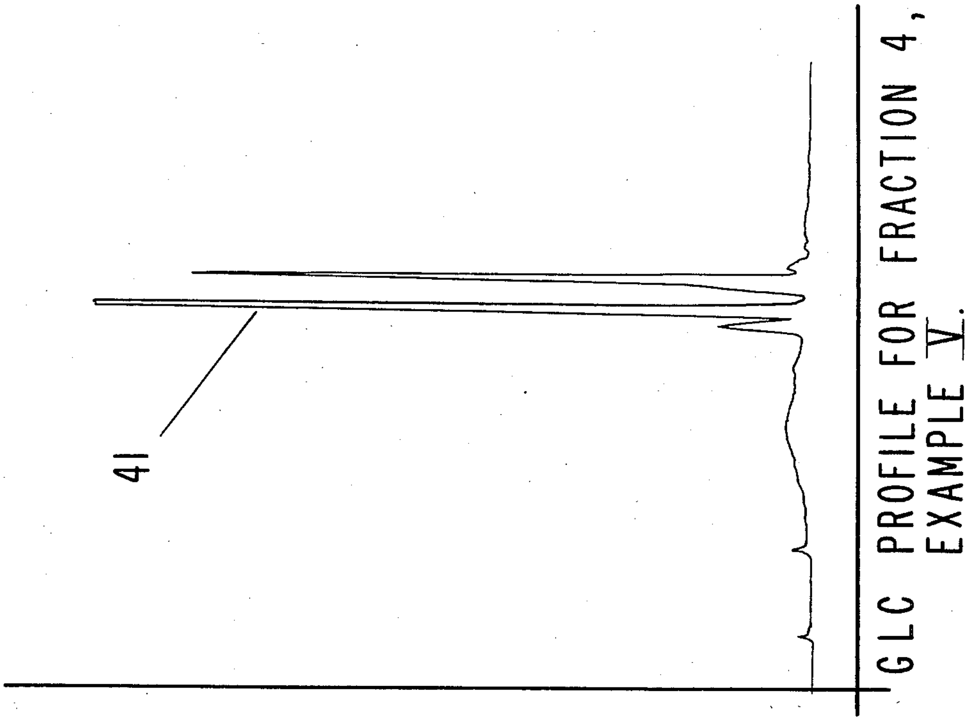

FIG. 3 is the GLC profile for Fraction 4 of the distillation of the reaction product of Example V containing the compound having the structure:

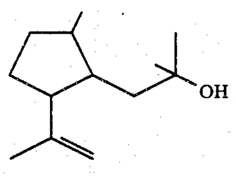

(Conditions: 8′×0.25″ 10% carbowax 20M column programmed at 100°–220° C. at 8° C. per minute).

Figure 4:
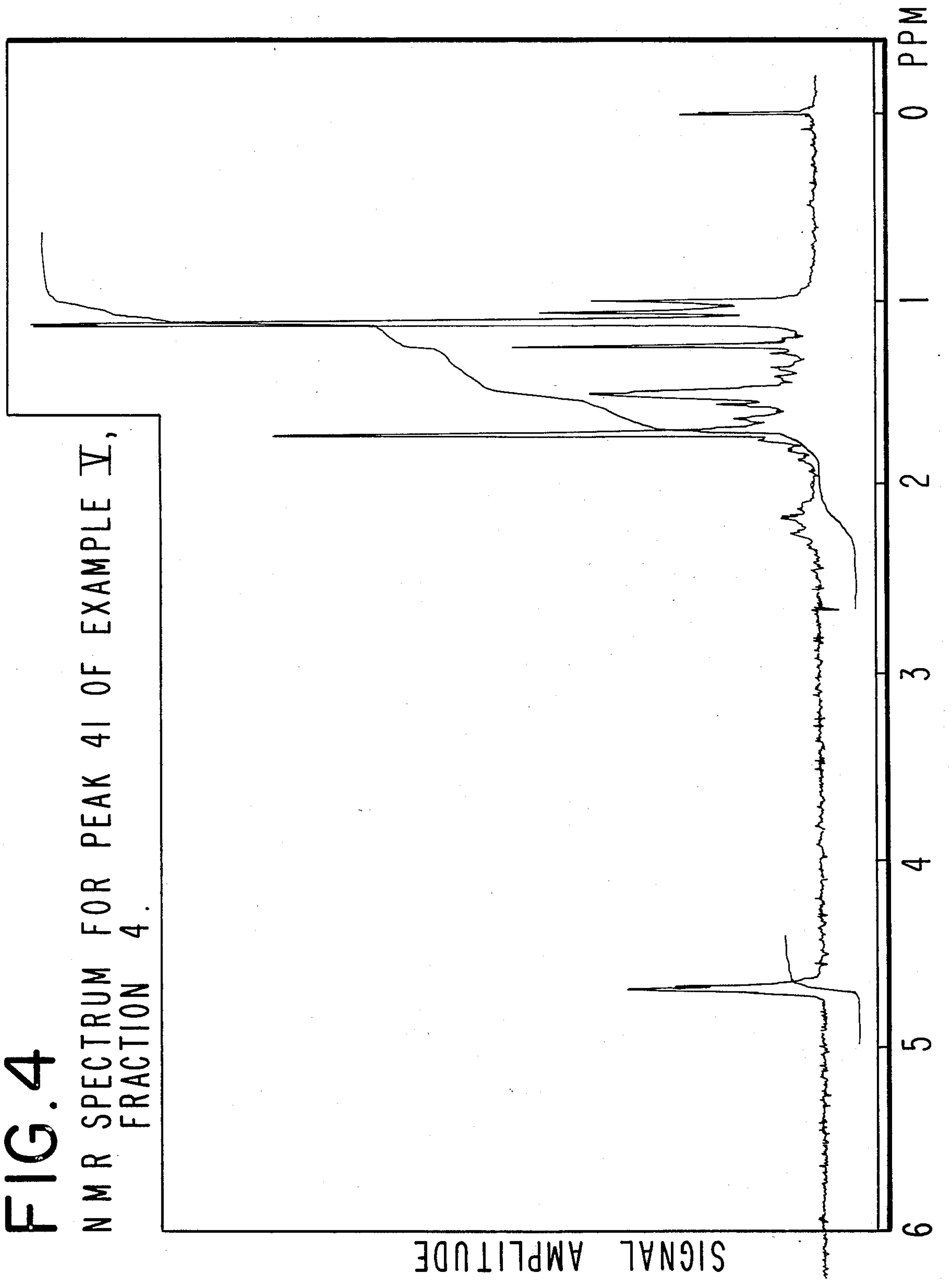

FIG. 4 is the NMR spectrum for the peak indicated by reference numeral 41 on the GLC profile of FIG. 3, taken from Fraction 4 of the distillation of the reaction product of Example V containing the compound having the structure:

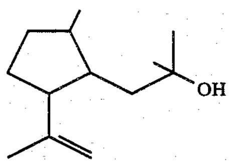

(Conditions: Field strength: 100 MHz; Solvent: $CFCl_3$).

Figure 5:
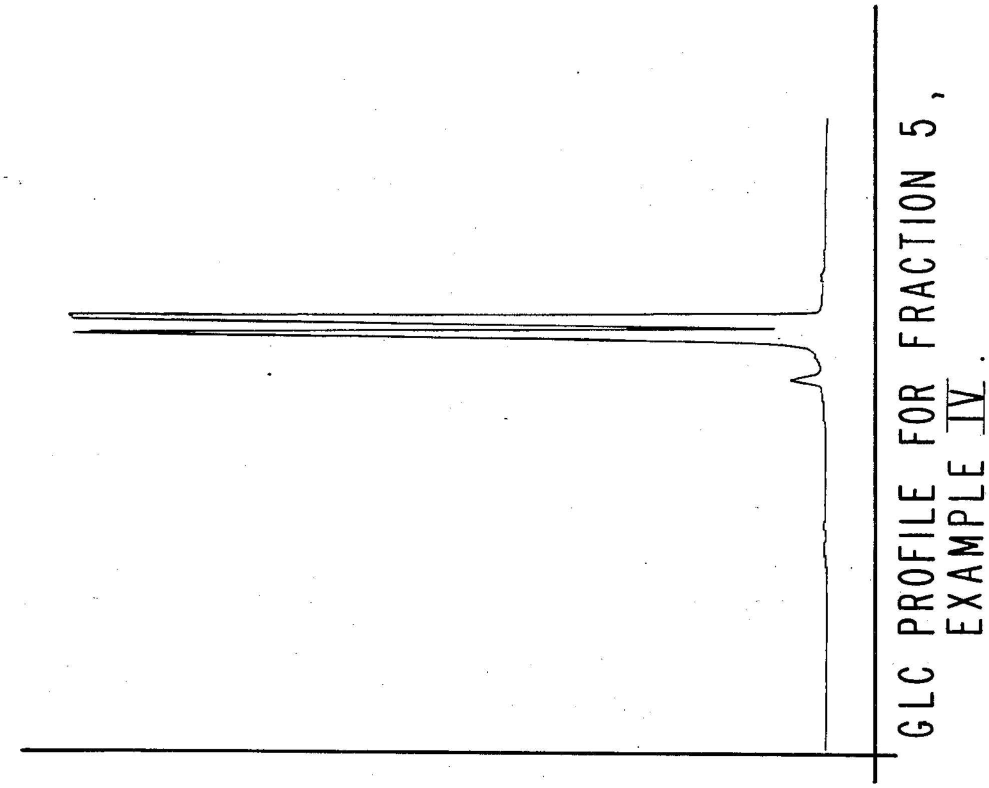

FIG. 5 is the GLC profile for Fraction 5 of the distillation of the reaction product of Example IV containing the compound having the structure:

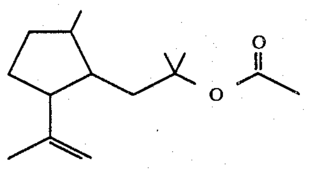

(Conditions: 8′×0.25″ 10% carbowax 20M column programmed at 100°–220° C. at 8° C. per minute).

Figure 6:
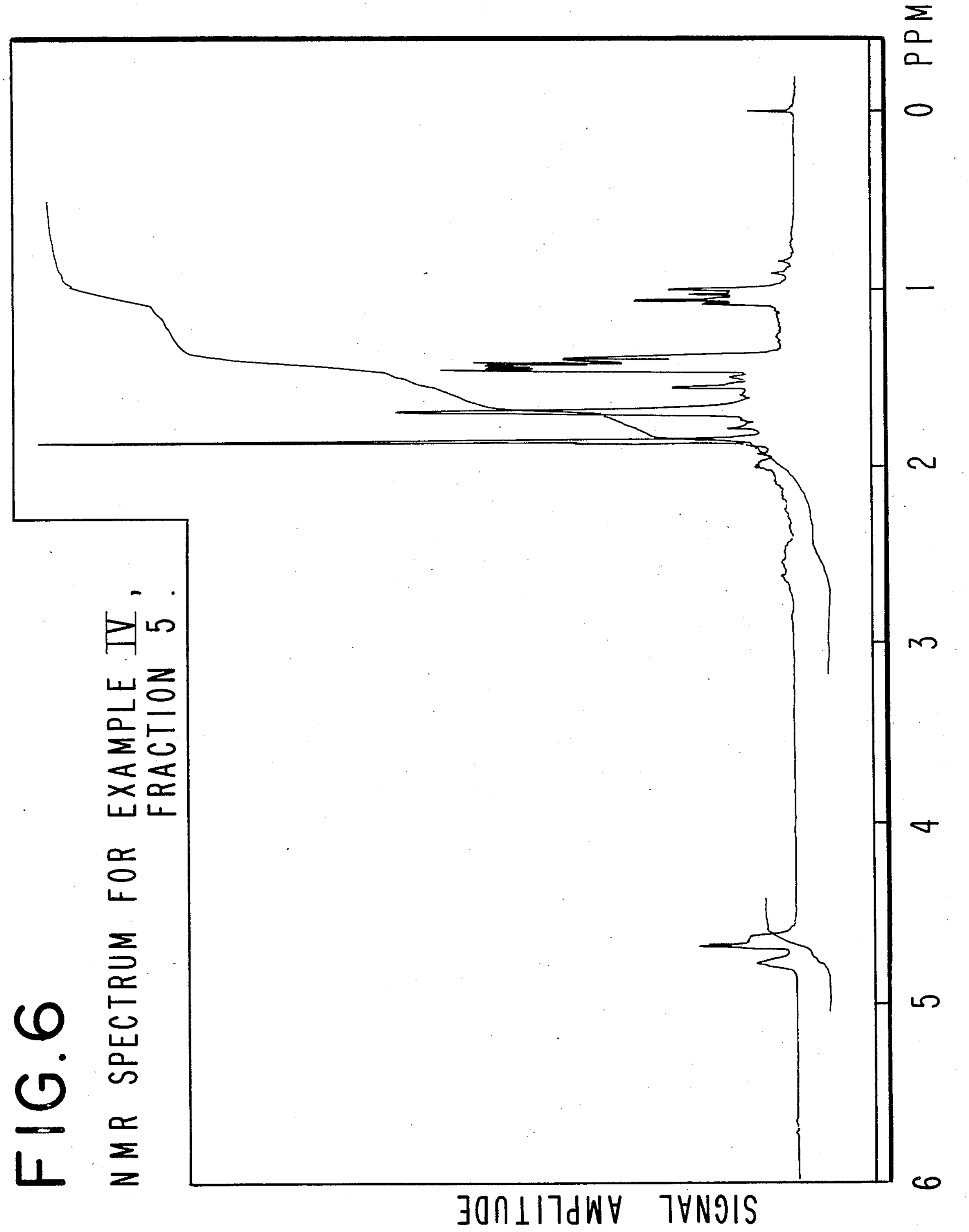

FIG. 6 is the NMR spectrum for Fraction 5 of the distillation of the reaction product of Example IV containing the compound having the structure:

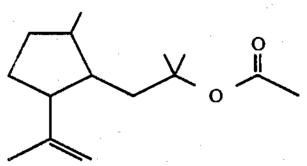

(Conditions: Field Strength: 100 MHz; Solvent: $CFCl_3$).

Figure 7:
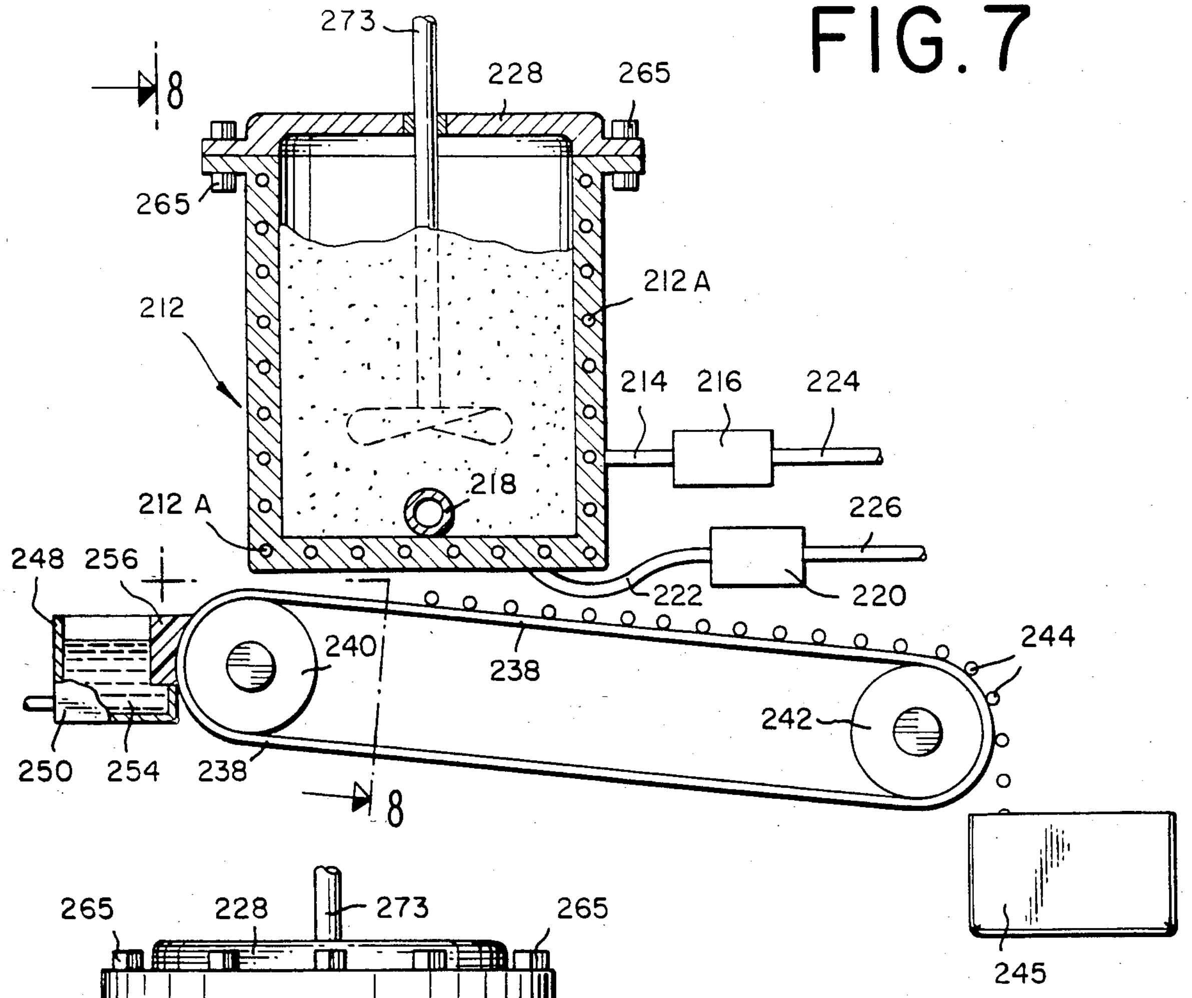

FIG. 7 is a cut-away side elevation view of apparatus used in preparing perfume-containing polymers of my invention, with the perfume being or containing at least one of the 2-isopropenyl-5-methylcyclopentanealkanols and esters thereof of my invention.

Figure 8:
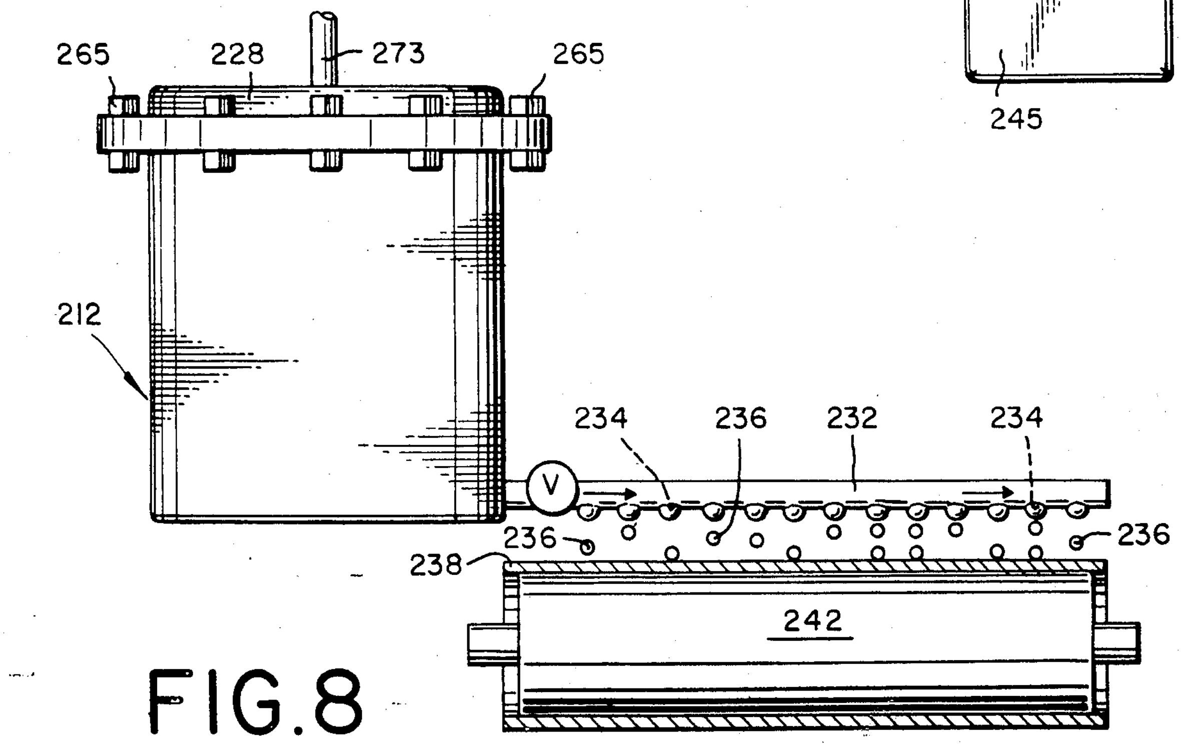

FIG. 8 is a cross-sectional view taken along lines 8—8 of FIG. 7.

DETAILED DESCRIPTION OF THE DRAWINGS

FIG. 3 is the GLC profile for Fraction 4 of the distillation of the reaction product of Example V containing the compound having the structure:

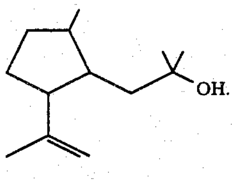

The peak indicated by reference numeral 41 is a peak for one of the isomers having the structures:

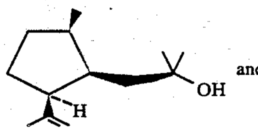

and

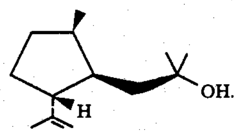

FIGS. 7 and 8 illustrate a preferred method for preparing compositions for the practice of my invention. A thermoplastic polymer, e.g., polyethylene is heated to about 220°–250° F. in a container 212 of the kind illustrated in FIGS. 7 and 8. A formulation containing fragrance (which includes at least one of the 2-isopropenyl-5-methylcyclopentanealkanols and esters thereof of my invention) is then quickly added to the liquified thermoplastic polymer. The lid 228 is put in place and the agitating means 273 is actuated. The temperature is maintained at about 225° F. and the mixing is continued for about 5–15 minutes. The valve "V" is then opened to allow flow of the molten thermoplastic polymer enriched with the fragrance containing at least one of the 2-isopropenyl-5-methylcyclopentanealkanols and esters thereof of my invention to exit through the orifices 234. The liquid falling through the orifices 234 solidifies almost instantaneously upon impact with moving cooled conveyor 238. The thermoplastic polymer beads or pellets 224 having pleasant aesthetically pleasing aromas are thus formed.

The conveyor 238 is moved using conveyor rollers 240 and 242. The vessel 212 is heated using heating coils 212A powered using power input supplies indicated by reference numerals 214, 216, 224, 222, 220 and 226. The solidified beads containing perfume compositions including at least one of the 2-isopropenyl-5-methylcyclopentanealkanols and esters thereof of my invention 244 travel into container 245 where they are used for subsequent processing. The conveyor is cooled using a cooling device indicated by reference numerals 248, 256, 250 and 254.

THE INVENTION

The present invention provides 2-isopropenyl-5-methylcyclopentanealkanols and esters thereof defined according to the structure:

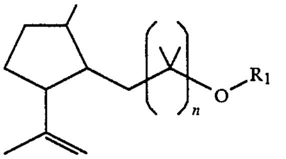

wherein $R_1$ represents hydrogen or $C_2$–$C_3$ acyl and n represents 0 or 1.

The present invention also provides processes for using such 2-isopropenyl-5-methylcyclopentanealkanols and esters thereof for their organoleptic properties in augmenting or enhancing the aromas of perfumes, colognes and perfumed articles (such as perfumed polymers, solid or liquid anionic, cationic, nonionic or zwitterionic detergents, soaps, fabric softener compositions, drier-added fabric softener articles such as BOUNCE ® registered trademark of the Procter & Gamble Company of Cincinnati, Ohio, fabric brighteners, cosmetic powders, bath preparations, hair preparations such as hair sprays and shampoos and the like).

The 2-isopropenyl-5-methylcyclopentanealkanols and esters thereof of my invention represented by the generic formula:

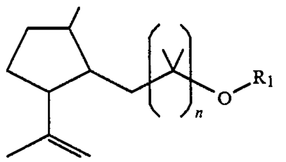

include "cis" and "trans" isomers as well as "optical" isomers thereof. Thus, for example, "cis" and "trans" isomers of the 2-isopropenyl-5-methylcyclopentanealkanols and esters thereof of my invention may be represented by the generic structures:

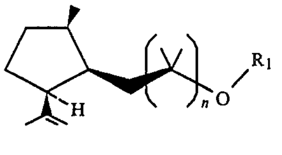

and

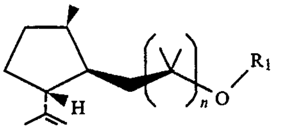

wherein n, and $R_1$ are defined, supra.

The 2-isopropenyl-5-methylcyclopentanealkanols and esters thereof of my invention may be prepared by first forming the Grignard reagent defined according to the structure:

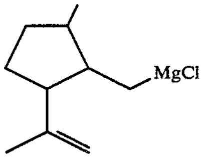

(a novel compound) by reacting dihydro myrcenyl chloride with magnesium in the presence of a suitable solvent according to the reaction:

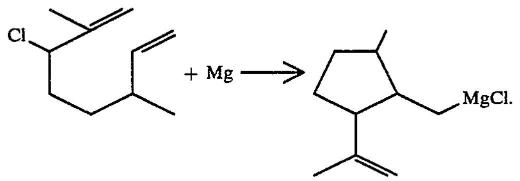

The Grignard reagent formation is carried out in the presence of an appropriate solvent such as anhydrous toluene or tetrahydrofuran. The mole ratio of magnesium to dihydro myrcenyl chloride varies from about 2:1 down to about 1:1 with a slight excess (e.g., 20 mole percent) of magnesium being preferred. The concentration of dihydro myrcenyl chloride in the solvent may vary from about 2 moles per liter up to about 6 moles per liter with a preferred concentration of about 3 moles per liter. The Griggnarg formation takes place at reflux conditions, preferably at a temperature in the range of from about 70° C. up to about 100° C., depending upon the particular solvent utilized.

The resulting Grignard reagent having the structure:

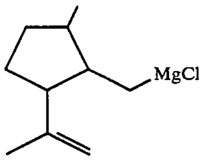

is then utilized as an intermediate in forming the several 2-isopropenyl-5-methylcyclopentanealkanols and esters thereof of my invention having the structure:

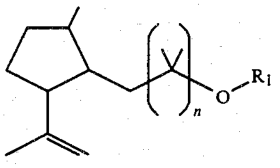

wherein $R_1$ is hydrogen or $C_2$–$C_3$ acyl and n represents 0 or 1.

Thus, the reagent may be oxidized using air in the presence of water vapor to form the compound having the structure:

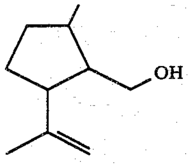

according the reaction:

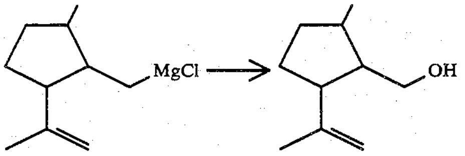

or it may be further reacted with acetone to form the salt having the structure:

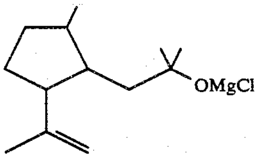

according to the reaction:

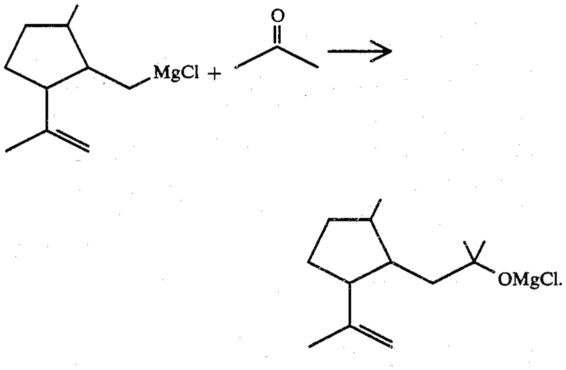

The resulting salt is then hydrolyzed in the presence of weak acid to form the alcohol having the structure:

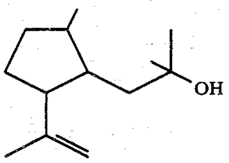

according to the reaction:

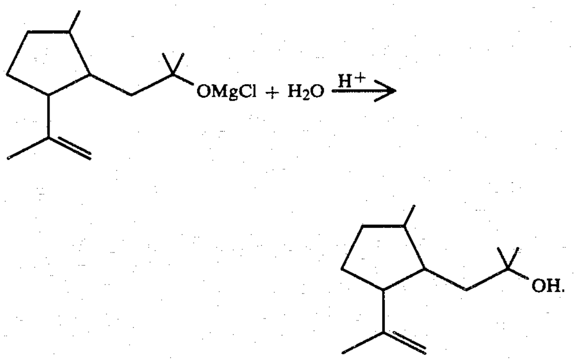

The reaction of the Grignard reagent having the structure:

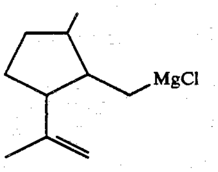

with air to form the alcohol having the structure:

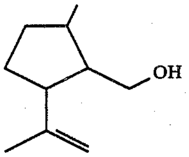

is carried out at a temperature in the range of from about 25° C. up to about 30° C. over a period of from about 4 up to about 10 hours with air being sparged through the reaction mass containing the Grignard reagent and solvent. At the end of the reaction, the reaction mass is "worked up" by filtering followed by washing with sodium chloride, acetic acid and sodium sulfite. The reaction mass is then distilled to yield the desired alcohol having the structure:

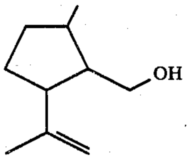

which is then used for organoleptic purposes or may be further reacted as by esterification.

The reaction of the Grignard reagent having the structure:

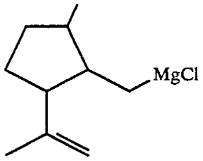

with acetone to form the salt having the structure:

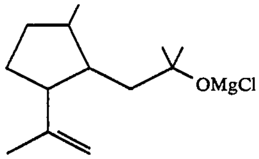

takes place at a temperature in the range of from about 25° C. up to about 40° C. External cooling is required for this reaction in view of the fact that it is an exothermic reaction. The reaction time is preferably in the range of from about 2 hours up to about 5 hours. At the end of the reaction, the reaction mass is filtered and hydrolyzed using weak acid, e.g., acetic acid and water. The organic layer is then dried using water and sodium bicarbonate solution and then fractionally distilled to yield the resulting alcohol having the structure:

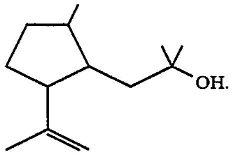

This alcohol may be used "as is" for its organoleptic properites or it may be esterified to form the appropriate acetic acid ester or propionic acid ester according to the esterficiation reactions as set forth, infra.

The resulting reaction products, of course, may be further separated into their specific position isomers defined, inter alia according to the structures:

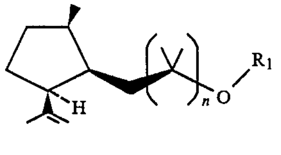

and

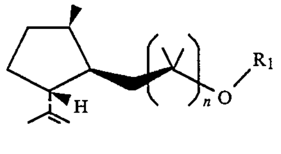

wherein $R_1$ and n are defined supra and more specifically, the structures:

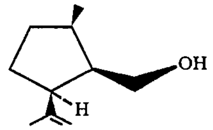
and
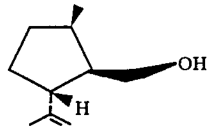

or:

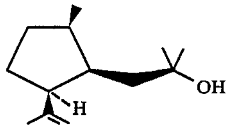
and
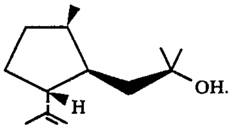

Another separation technique for separating such isomers is high performance liquid chromatography (HPLC).

The resulting alcohols having the structures:

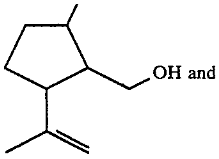
and
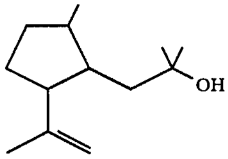

may, if desired, be esterified. Thus, for example, the alcohol having the structure:

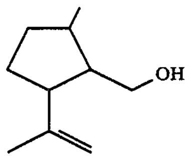

may be reacted with propionic anhydride in order to form the ester having the structure:

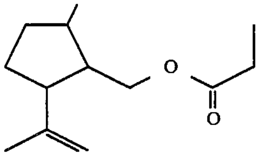

according to the reaction:

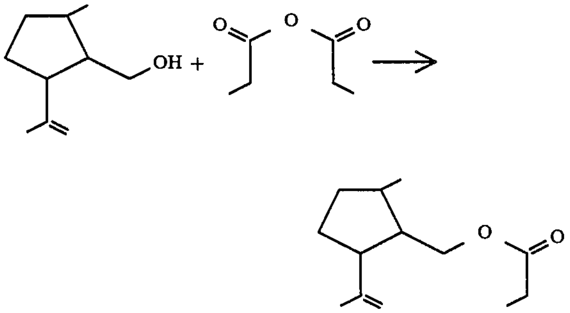

and the compound having the structure:

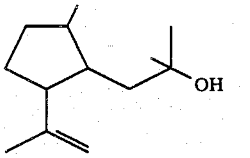

may be esterified with acetic anhydride to form the compound having the structure:

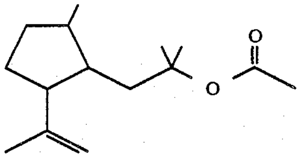

according to the reaction:

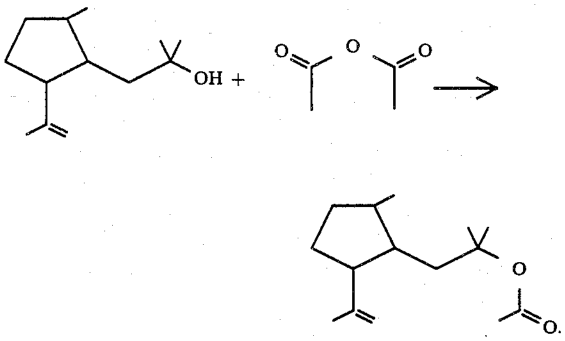

The conditions for esterification are standard esterification conditions.

Thus, the reaction of the compound having the structure:

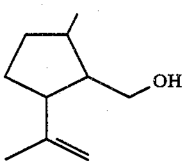

with propionic anhydride is carried out at reflux conditions, e.g., 110° C. over a period of between about 5 and about 10 hours. At the end of the reaction, the reaction mass is mixed with water and the aqueous phase is extracted with an inert solvent such as toluene. The organic phases are combined and the resulting combined organics are then, again, washed with water and then fractionally distilled. Odor-acceptable fractions are then combined and utilized for their organoleptic properties.

By the same token, for example, the alcohol having the structure:

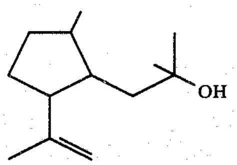

may be reacted with acetic anhydride according to the reaction:

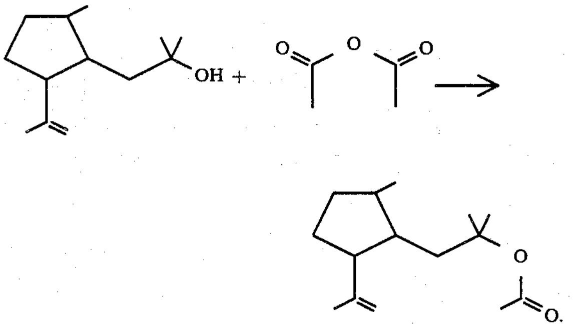

This reaction is carried out in the presence of a sodium acetate catalyst. The mole ratio of acyl anhydride:alcohol in both reactions is between 3:1 down to about 2:1.

The reaction mass is then refluxed at a temperature of about 110° C. for a period of from about 5 up to about 10 hours. At the end of the esterification reaction, the reaction mass is mixed with water and the organic phase is washed with toluene. The organics are then combined and rewashed with water and aqueous sodium bicarbonate. The resulting product is then fractionally distilled to yield the product having the structure:

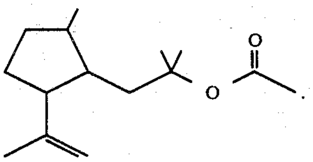

The odor-acceptable fractions are then bulked for subsequent organoleptic uses.

Table I, set forth below indicates the structures of the particular 2-isopropenyl-5-methylcyclopentanealkanols and esters thereof of my invention and their specific organoleptic properties:

TABLE I

| Structure of 2-Isopropenyl-5-Methyl-cyclopentanealkanols And Esters Thereof | Aroma Properties |
| --- | --- |
| 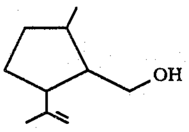 | A piney, woody, camphoraceous, minty and rosy aroma with eucalyptus topnotes. |

TABLE I-continued

| Structure of 2-Isopropenyl-5-Methylcyclopentanealkanols And Esters Thereof | Aroma Properties |
|---|---|
| 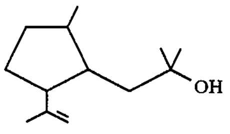 | A woody and camphoraceous aroma with sweaty topnotes. |
| 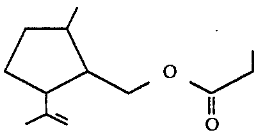 | A woody, peppery, spicy, green, violet aroma with carnation green and ambery topnotes. |
| 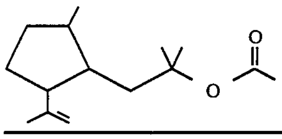 | A woody, ambery, camphoraceous and vetiver aroma profile with cedarwood topnotes. |

The 2-isopropenyl-5-methylcyclopentanealkanols and esters thereof of my invention can be used to contribute piney, woody, camphoraceous, minty, rosy, peppery, spicy, green, violet, ambery and vetiver aromas with eucalyptus, sweaty, carnation, green, ambery and cedarwood topnotes to perfume compositions, colognes and perfumed articles such as solid or liquid cationic, anionic, nonionic or zwitterionic detergents, perfumed polymers, fabric softener compositions, fabric softener articles, optical brighteners, fabric conditioners, hair preparations, shampoos and hair sprays. As olfactory agents, the 2-isopropenyl-5-methylcyclopentanealkanols and esters thereof of my invention can be formulated into or used as components of a "perfume composition".

The term "perfume composition" is used herein to mean a mixture of organic compounds including, for example, alcohols, other than the alcohols of my invention, aldehydes, ketones, nitriles, ethers, lactones, esters other than the esters of my invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual 2-isopropenyl-5-methylcyclopentanealkanols and esters thereof of this invention or mixtures thereof can be used to alter the aroma characteristics of the perfume composition, for example, by highlighting or moderating the olfactory reaction contributed by another ingredient in the composition.

The amount of the 2-isopropenyl-5-methylcyclopentanealkanols and esters thereof of my invention which will be effective in perfume compositions depends upon many factors including the other ingredients, their amounts and the effects which are desired. It has been found that perfume compositions containing as little as 0.1 percent of at least one of the 2-isopropenyl-5-methylcyclopentanealkanols and esters thereof of my invention or even less and perfume compositions containing as much as 70 percent of at lease one of the 2-isopropenyl-5-methylcyclopentanealkanols and esters thereof of my invention can be used to impart interesting piney, woody, camphoraceous, minty, rosy, peppery, spicy, green, violet, ambery and vetiver aromas with eucalyptus, sweaty, carnation, green, ambery and cedarwood topnotes to perfumed articles, perfume compositions and colognes.

Such "perfumed articles" include fabric softener compositions, drier-added fabric softener articles, cosmetic powders, talcs, solid or liquid anionic, cationic, nonionic or zwitterionic detergents and perfumed polymers. The amounts employed can range up to 70 percent and will depend on considerations of cost, nature of the end product and the effect desired on the finished product and particular fragrance sought.

Thus, one or more of the 2-isopropenyl-5-methylcyclopentanealkanols and esters thereof of my invention can be used alone or in a perfume composition as an olfactory component, in solid or liquid anionic, cationic, nonionic or zwitterionic detergents (including hand soaps), perfumed polymers (those which may be microporous, those which may be macroporous, and those which may contain, if desired, particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer or a polymer containing an absorbent filler or a perfumed article such as a solid or liquid anionic, cationic, nonionic or zwitterionic detergent or a cosmetic powder, as little as 0.01% of at least one of the 2-isopropenyl-5-methylcyclopentanealkanols and esters thereof of my invention will suffice to provide an interesting piney, woody, camphoraceous, minty, rosy, peppery, spicy, green, violet, ambery and vetiver aroma with eucalyptus, sweaty, carnation, green, ambery and cedarwood topnotes. Generally, no more than 0.8 percent of at least one of the 2-isopropenyl-5-methylcyclopentanealkanols and esters thereof of my invention is required in the perfumed article. Accordingly, the range of at least one of the 2-isopropenyl-5-methylcyclopentanealkanols and esters thereof in perfumed articles for the purposes of my invention is from about 0.01 percent up to about 0.8 percent.

In addition, the perfume compositions of my invention can contain a vehicle or carrier for the 2-isopropenyl-5-methylcyclopentanealkanols and esters thereof of my invention alone or with other ingredients. The vehicle can be a liquid such as an alcohol such as ethanol, a glycol such as propylene glycol or the like. The carrier can be an absorbent solid such as a gum (e.g., xanthan gum, guar gum or gum arabic) or components for encapsulating the composition as by coacervation (using gelatin) or by forming a polymer wall around a liquid center, e.g., using a urea formaldehyde prepolymer to form a polymeric wall around the liquid perfume center.

When incorporating at least one of the 2-isopropenyl-5-methylcyclopentanealkanols and esters thereof of my invention into polymers, various techniques well known to those having ordinary skill in the art may be used. Thus, the 2-isopropenyl-5-methylcyclopentanealkanols and esters thereof of my invention may be admixed with a molten polymer such as polyethylene or polypropylene and the resulting mixture may be formed into pellets which are used as a polymer concentrate. In the alternative, at least one of the 2-isopropenyl-5-methylcyclopentanealkanols and esters thereof of my invention taken alone or further in combination with other perfume ingredients may be blended into a polymer during an extrusion operation using a single screw or twin screw extruder. When using an extruder, polymers of ethylene, propylene, ethylene/vinyl acetate copolymers and poly(epsilon caprolactone) as well as various nylons, e.g., Nylon-6 may be used.

The following Examples I–VI set forth processes for preparing the 2-isopropenyl-5-methylcyclopentanealkanols and esters thereof of my invention. The following Examples VII, et seq. represent methods for using the 2-isopropenyl-5-methylcyclopentanealkanols and esters thereof of my invention for their organoleptic properties.

The 2-isopropenyl-5-methylcyclopentanealkanols and esters thereof of my invention having the structure:

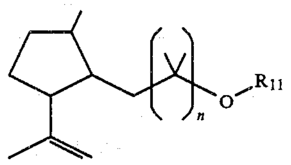

wherein n represents 0 or 1 and $R_{11}$ represents $C_2$–$C_3$ acyl are novel compounds.

EXAMPLE I

PREPARATION OF 2-ISOPROPENYL-5-METHYLCYCLOPENTANE METHANOL

Reactions

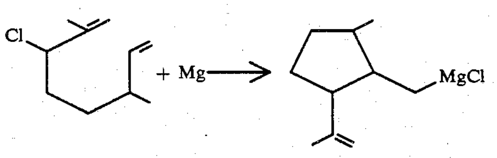

and

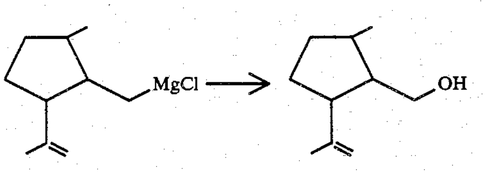

Into a 3 liter reaction vessel equipped with stirrer, thermometer, reflux condenser, heating mantle and cooling coils as well as a nitrogen blanket apparatus is placed 120 grams of magnesium turnings and a mixture (premixed) of 900 grams toluene and 600 grams tetrahydrofuran. 2 Grams of dibromoethane is added to the reaction vessel with stirring to initiate the Grignard reaction, together with 25 grams of dihydromyrcenyl chloride (73%).

The reaction mixture is heated to reflux (70° C.) and over a period of 2 hours, 917 grams (in order to make up 4 moles) of 73% dihydromyrcenyl chloride is added to the reaction mass with stirring at reflux. The reaction mass is then refluxed at 80°–88° C. for a period of 2 hours.

At this point in time the compound having the structure:

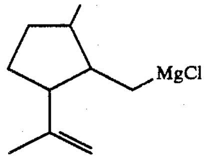

is formed.

Dried air (produced by means of directing air through a column of "DRI-RITE®" is sparged through a fritted glass dispersion tube mounted near the bottom of the reaction mass. The addition of air to the reaction mass is exothermic and the reaction mass is maintained at 25°–30° C. with a cooling bath. The sparging of air continues for a period of 6 hours.

At this point in time the compound having the structure:

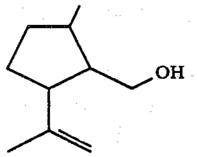

has been produced.

The reaction mass is filtered and the filtrate is split into two parts (each weighing 953 grams). The first filtrate fraction is washed with one 3000 cc portion of 10% aqueous sodium chloride and 125 ml acetic acid followed by one 1000 cc portion of 10% aqueous sodium chloride. The other half is washed with aqueous saturated sodium sulfite. The two filtrate fractions are combined and distilled on a 12" column packed with saddles yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 75 | 85 | 3.8 | 2:1 | 58.3 |
| 2 | 72 | 90 | 3.0 | 9:1 | 22.3 |
| 3 | 72 | 90 | 3.0 | 9:1 | 20.5 |
| 4 | 72 | 90 | 3.0 | 9:1 | 20.9 |
| 5 | 72 | 90 | 3.0 | 9:1 | 20.0 |
| 6 | 73 | 92 | 2.9 | 9:1 | 17.8 |
| 7 | 73 | 93 | 2.9 | 9:1 | 15.1 |
| 8 | 73 | 95 | 2.9 | 9:1 | 12.3 |
| 9 | 73 | 99 | 3.0 | 9:1 | 17.1 |
| 10 | 73 | 108 | 3.0 | 9:1 | 16.0 |
| 11 | 73 | 125 | 3.0 | 9:1 | 10.0. |

Bulked fractions 3–11 have a piney, woody, camphoraceous minty and rosy aroma with eucalyptus topnotes.

Figure 1:
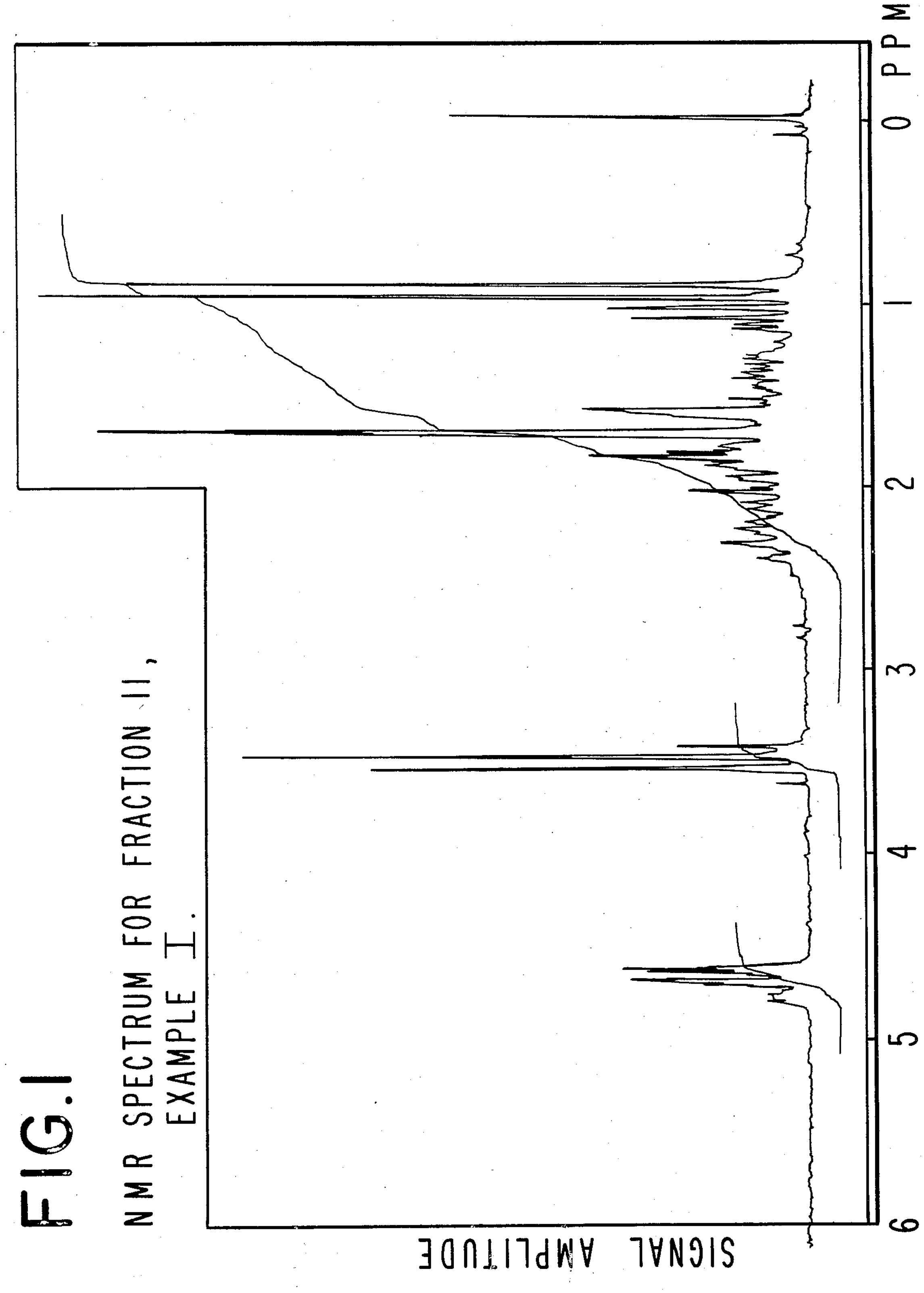
FIG. 1 is the NMR spectrum for Fraction 11 of the distillation of the reaction product of Example I containing the compound having the structure.

FIG. 1 is the NMR spectrum for fraction 11 of the foregoing distillation containing the compound having the structure:

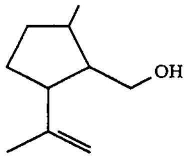

(Conditions: Field strength: 100 MHz; Solvent: $CFCl_3$). and more specifically, containing 70% by weight of the compound having the structure:

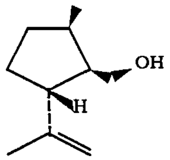

and 15% by weight of the compound having the structure:

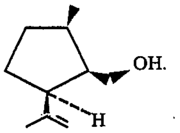

(Conditions: Field strength: 100 MHz; Solvent: $CFCl_3$).

EXAMPLE II

PREPARATION OF THE PROPIONIC ACID ESTER OF 2-ISOPROPENYL-5-METHYLCYCLOPENTANE METHANOL

Reaction

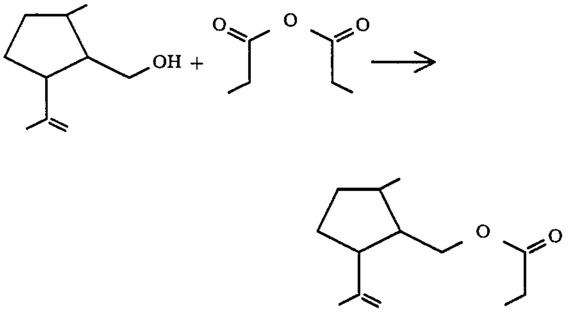

Into a 1 liter reaction flask equipped with stirrer, thermometer, reflux condenser and addition funnel is placed 300 grams of propionic anhydride (2.3 moles). The propionic anhydride is heated to 110° C. and, with stirring, over a period of 30 minutes Fraction 2 of the distillation product of Example I which is the alcohol having the structure:

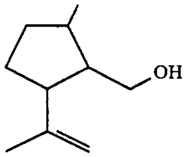

is added over a 30 minute period.

The stirring of the reaction mass is continued at a temperature of 110° C. for another 6.5 hours. At the end of the 6.5 hour period, the reaction mass is cooled to 60° C. and 200 ml water is added over a 10 minute period. The reaction mass is then stirred for a period of 30 minutes at 60° C. The organic phase is separated from the aqueous phase. The aqueous phase is extracted with 75 ml toluene and the toluene extract is combined with the organic phase. The organic phase is then washed with two 75 ml portions of water. The organic phase is then fractionated on a 12"×1" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 20 | 80 | 50.0 | 2:1 | 24.7 |
| 2 | 86 | 100 | 2.4 | 4:1 | 25.3 |
| 3 | 87 | 101 | 2.4 | 4:1 | 17.4 |
| 4 | 88 | 102 | 2.4 | 4:1 | 20.6 |
| 5 | 88 | 102 | 2.4 | 9:1 | 16.4 |
| 6 | 89 | 102 | 2.4 | 4:1 | 15.5 |
| 7 | 90 | 103 | 2.6 | 4:1 | 18.5 |
| 8 | 90 | 103 | 2.6 | 4:1 | 18.1 |
| 9 | 91 | 104 | 2.6 | 4:1 | 18.5 |
| 10 | 92 | 104 | 2.6 | 9:1 | 13.0 |
| 11 | 92 | 104 | 2.6 | 9:1 | 16.6 |
| 12 | 94 | 108 | 2.6 | 9:1 | 9.7 |
| 13 | 96 | 118 | 2.6 | 9:1 | 12.5 |
| 14 | 94 | 220 | 2.6 | 9:1 | 8.6. |

The resulting product having the structure:

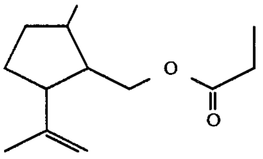

has a woody, peppery, spicy, green and violet aroma with carnation, green and ambery topnotes.

FIG. 2 is the NMR spectrum for Fraction 10 of the foregoing distillation containing the compound having the structure:

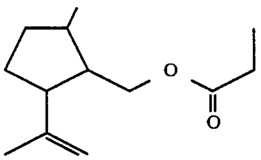

(Conditions: Field strength: 100 MHz; Solvent: $CFCl_3$).

EXAMPLE III

PREPARATION OF 2-ISOPROPENYL-α,α,5-TRIMETHYLCYCLOPENTANE ETHANOL

Reactions

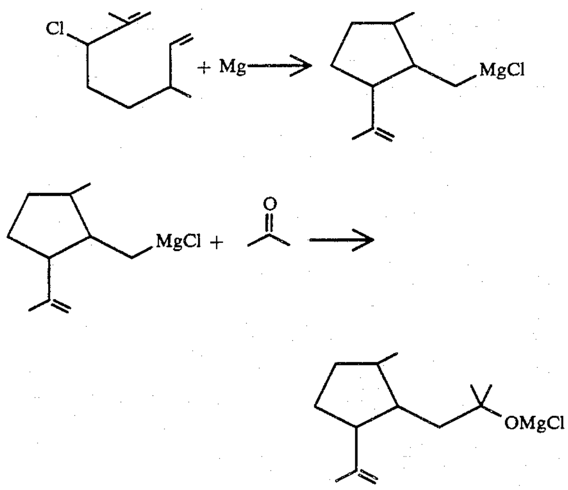

and

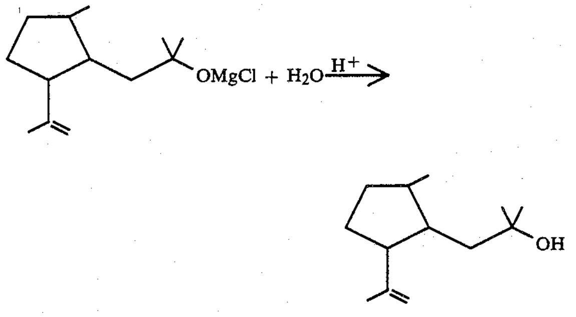

Into a 5 liter reaction vessel equipped with stirrer, thermometer, nitrogen blanket apparatus, heating mantle and addition funnel is placed 500 cc of a premixture of 900 grams toluene and 600 grams tetrahydrofuran. To this mixture, 120 grams (5 moles) of magnesium is added. The Grignard reaction initiator, dibromoethane (2 grams) and 25 grams of dihydromyrcenyl chloride is then added while maintaining the reaction mass at 60° C. Over 10 minutes, the remainder of the toluene-tetrahydrofuran mixture is added to the reaction flask.

While maintaining the reaction temperature at 70°-85° C., over a period of 4 hours, 917 grams of dihydromyrcenyl chloride (73%) is added to the reaction mass. At the end of the 4 hour period, the reaction mass is continued to be refluxed at 85° C. for a period of 2 hours. At the end of this 2 hour period, the reaction mass is cooled to 30° C. and, while maintaining the reaction mass at 30° C. over a period of 1 hour, 260 grams (4.5 moles) of acetone is added to the reaction mass.

The reaction mass is then stirred for an additional 3 hours at 30° C.

The reaction mass is then filtered (to remove excess magnesium metal) and the filtrate is poured onto 500 grams ice, 1.5 Liters water and 300 grams of acetic acid is added to the mixture. The organic phase is separated from the aqueous phase and the organic phase is washed with one 1 liter portion of water and one 1 liter portion of 5% aqueous sodium bicarbonate.

The resulting product is then distilled on a 12" column packed with saddles yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 80 | 98 | 250.0 | 1,191.7 |
| 2 | 80 | 90 | 75.0 | 233.0 |
| 3 | 80 | 85 | 4.0 | 111.5 |
| 4 | 108 | 122 | 2.4 | } 430.6 |
| 5 | 110 | 130 | 2.2 | |

Fractions 4 and 5 are then bulked and distilled on a 12"×1.5" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 65 | 90 | 2.4 | 9:1 | 26.1 |
| 2 | 67 | 92 | 2.4 | 9:1 | 39.3 |
| 3 | 72 | 93 | 2.4 | 9:1 | 22.3 |
| 4 | 77 | 94 | 2.4 | 9:1 | 29.6 |
| 5 | 80 | 95 | 2.4 | 9:1 | 35.3 |
| 6 | 80 | 95 | 2.4 | 9:1 | 33.4 |
| 7 | 82 | 97 | 2.4 | 9:1 | 37.2 |
| 8 | 83 | 98 | 2.4 | 9:1 | 32.8 |
| 9 | 83 | 101 | 2.4 | 9:1 | 95.4 |
| 10 | 83 | 125 | 2.4 | 9:1 | 49.1 |
| 11 | 117 | 227 | 2.4 | 9:1 | 43.4. |

The resulting product having the structure:

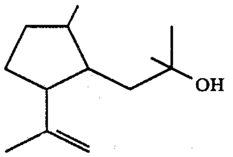

has a woody and camphoraceous aroma with sweaty topnotes.

FIG. 3 is the GLC profile for Fraction 4 of the foregoing distillation. The peak indicated by reference numeral 41 is the peak for the isomers having the structures;

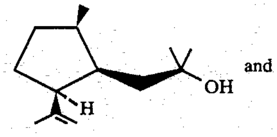

and

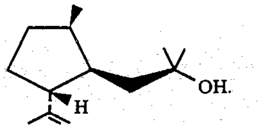

FIG. 4 is the NMR spectrum for the peak indicated by reference numeral 41 of FIG. 3 which is the GLC profile of Fraction 4 of the foregoing distillation. The peak contains the compounds having the structures:

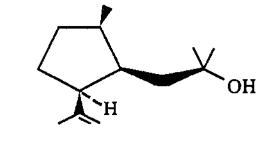
and
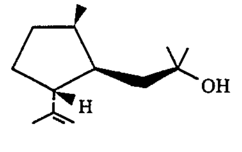

(Conditions: Field strength: 100 MHz; Solvent: $CFCl_3$).

EXAMPLE IV

PREPARATION OF THE ACETIC ACID ESTER OF 2-ISOPROPENYL-α,α,5-TRIMETHYLCYCLOPENTANE ETHANOL

Reaction

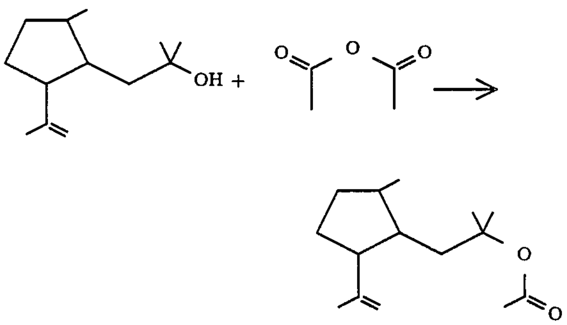

Into a 1 liter reaction flask equipped with stirrer, thermometer, reflux condenser and heating mantle are placed 230 grams of bulked Fractions 4–10 of the alcohol produced according to Example III having the structure:

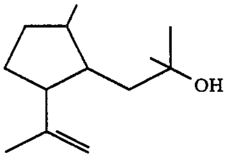

(1.17 moles); 275 grams (2.7 moles) of acetic anhydride and 22 grams of sodium acetate. The reaction mass is stirred for a period of 7 hours maintaining the temperature thereof at 110° C.

At the end of the 7 hour period, the reaction mass is cooled to 75° C. and 200 cc of water is added. The resulting mixture is stirred for 30 minutes. 150 ml Toluene is then added with stirring. The organic phase is separated from the aqueous phase. The organic phase is then washed with one 200 cc portion of water followed by one 250 cc portion of 5% aqueous sodium bicarbonate followed by one 200 cc portion of water.

The reaction mass is then distilled on a 12"×1.5" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 28 | 78 | 7.0 | 1:1 | 81.0 |
| 2 | 77 | 102 | 2.0 | 9:1 | 19.5 |
| 3 | 85 | 104 | 2.0 | 9:1 | 23.8 |
| 4 | 86 | 105 | 2.0 | 9:1 | 27.4 |
| 5 | 87 | 105 | 2.0 | 9:1 | 24.6 |
| 6 | 87 | 106 | 2.0 | 9:1 | 19.0 |
| 7 | 87 | 107 | 2.0 | 4:1 | 54.3 |
| 8 | 87 | 117 | 2.0 | 4:1 | 41.5 |
| 9 | 85 | 200 | 2.0 | 4:1 | 21.0. |

The resulting product having the structure:

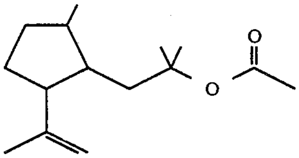

has a woody, ambery, camphoraceous and vetiver aroma with cedarwood topnotes.

FIG. 5 is the GLC profile for Fraction 5 of the foregoing distillation (Conditions: 8'×0.25" 10% carbowax 20M column programmed at 100°–220° C. at 8° C. per minute).

FIG. 6 is the NMR spectrum for Fraction 5 of the foregoing distillation containing the compound having the structure:

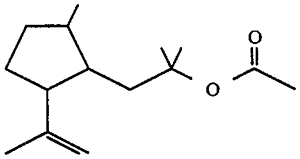

(Conditions: Field strength: 100 MHz; Solvent: $CFCl_3$).

EXAMPLE V

PREPARATION OF 2-ISOPROPENYL-α,α,5-TRIMETHYLCYCLOPENTANE ETHANOL

Reactions

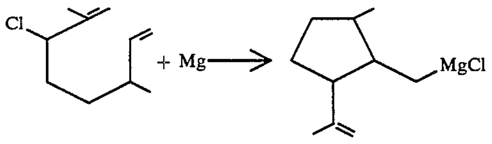

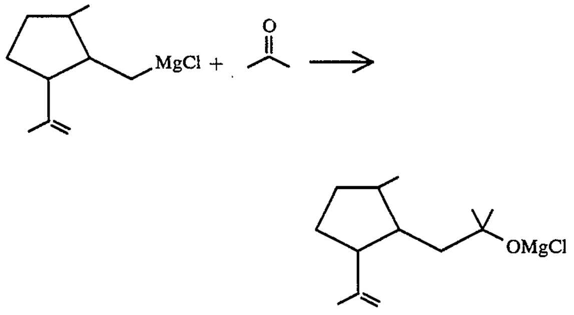

and

-continued

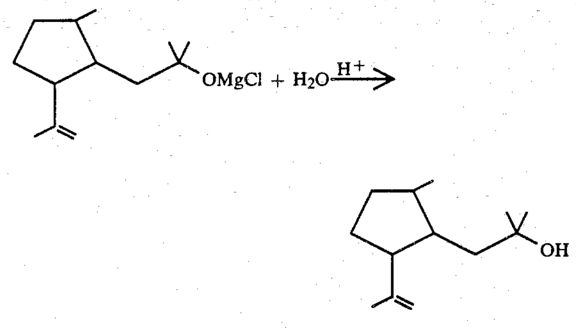

This example is substantially the same as Example III except that during the preparation of the Grignard reagent having the structure:

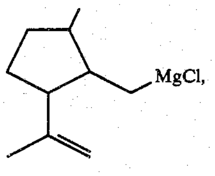

the reaction temperature is maintained at 65°-70° C.

The same procedure and apparatus is used as in Example III. The total amount of dihydromyrcenyl chloride (72%) used is 773 grams. The total amount of magnesium turnings used is 98 grams. The total amount of toluene used is 720 grams. The total amount of tetrahydrofuran used is 480 grams. The total amount of acetone used is 208 grams. The reaction to form the Grignard reagent as stated, supra is carried out at 65°-70° C. over a period of 4 hours. The reaction mass is then aged for 2 hours. The reaction mass is then cooled to 30° C. and over a period of 1 hour, 208 grams of acetone is added. The reaction mass is then aged for a period of 2 hours.

The reaction mass is then filtered to remove the magnesium and placed into a separatory funnel containing 300 grams of acetic acid, 500 grams of ice and 1.5 liters of water. The organic phase is separated from the aqueous phase and the organic phase is washed with 1 liter of water followed by 1 liter of 5% aqueous sodium bicarbonate.

The resulting product is distilled on a 1"×12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 75 | 100 | 3.0 | 9:1 | 15.3 |
| 2 | 77 | 100 | 3.0 | 9:1 | 20.7 |
| 3 | 81 | 101 | 3.0 | 9:1 | 23.4 |
| 4 | 85 | 102 | 3.0 | 9:1 | 17.1 |
| 5 | 88 | 102 | 3.0 | 19:1 | 14.7 |
| 6 | 88 | 103 | 3.0 | 19:1 | 15.2 |
| 7 | 89 | 104 | 3.0 | 19:1 | 19.1 |
| 8 | 89 | 104 | 3.0 | 19:1 | 22.6 |
| 9 | 89 | 106 | 3.0 | 19:1 | 17.6 |
| 10 | 89 | 108 | 3.0 | 19:1 | 22.4 |
| 11 | 89 | 109 | 3.0 | 19:1 | 23.3 |
| 12 | 89 | 110 | 3.0 | 19:1 | 19.7 |
| 13 | 88 | 115 | 2.9 | 19:1 | 13.0 |
| 14 | 90 | 120 | 3.0 | 19:1 | 25.4 |
| 15 | 89 | 130 | 2.8 | 19:1 | 23.4 |
| 16 | 89 | 143 | 2.8 | 19:1 | 20.5 |
| 17 | 128 | 155 | 2.8 | 19:1 | 19.5 |
| 18 | 130 | 158 | 2.8 | 19:1 | 19.1. |

The resulting product has the structure:

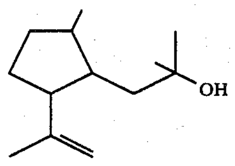

and has a woody, camphoraceous aroma with sweaty topnotes.

EXAMPLE VI

PREPARATION OF THE ACETIC ACID ESTER OF 2-ISOPROPENYL-α,α,5-TRIMETHYLCYCLOPENTANE ETHANOL

Reaction

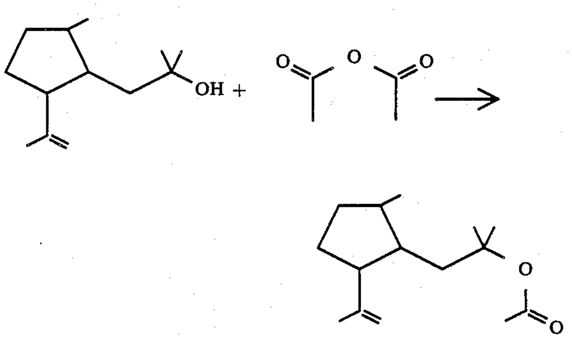

Into a 3 neck flask equipped with stirrer, thermometer, heating mantle and addition funnel is placed 184 grams of bulked Fractions 6, 7, 13, 14, 15 and 16 of the distillation product of Example V consisting essentially of the compound having the structure:

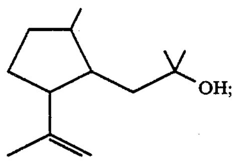

220 grams acetic anhydride and 18 grams sodium acetate. The reaction mass is heated to 110° C. with stirring and maintained at 110° C. for a period of 7 hours.

At the end of the 7 hour period, the sodium acetate is filtered and the filtrate is washed with one 200 cc portion of water followed by one 250 cc portion of aqueous 5% sodium carbonate followed by one 200 cc portion of water. The resulting product is then distilled on a 10" splash column yielding the following fractions:

| Fraction No. | Vapor Temp. (°C.) | Liquid Temp. (°C.) | Vacuum mm/Hg. Pressure |
|---|---|---|---|
| 1 | 13/18 | 85/92 | 50/50 |
| 2 | 60 | 100 | 14.0 |
| 3 | 104 | 120 | 24.0 |
| 4 | 100 | 122 | 1.6 |
| 5 | 95 | 125 | 2.0. |

Fractions 2-5 are bulked and redistilled on a 1" shale head column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 53/85 | 100/104 | 2.0 | 9:1 |
| 2 | 95 | 106 | 2.0 | 9:1 |
| 3 | 94 | 105 | 2.0 | 9:1 |
| 4 | 94 | 105 | 1.8 | 9:1 |
| 5 | 95 | 108 | 1.8 | 9:1 |
| 6 | 95 | 109 | 1.8 | 9:1 |
| 7 | 95 | 111 | 1.8 | 9:1 |
| 8 | 95 | 123 | 1.8 | 9:1 |
| 9 | 95 | 150 | 1.8 | 9:1 |
| 10 | 95 | 158 | 1.8 | 9:1. |

The resulting product having the structure:

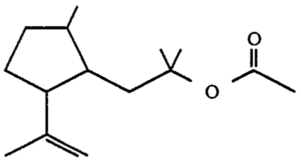

has a woody, ambery, camphoraceous, vetiver aroma with cedarwood topnotes.

EXAMPLE VII

FRAGRANCE COMPOSITIONS

The following woody/amber/cedarwood perfume compositions are prepared as follows:

| Ingredients | Parts by Weight VII (A) | VII (B) | VII (C) | VII (D) |
|---|---|---|---|---|
| Vetiver Oil Venezuela | 8 | 8 | 8 | 8 |
| Cedryl Methyl Ether | 4 | 4 | 4 | 4 |
| Isocyclemone E (Trademark of International Flavors & Fragrances Inc. of New York, New York; produced according to the process of U.S. Letters Pat. No. 3,911,018 | 12 | 12 | 12 | 12 |
| Fixateur 404 (Trademark of Firmenich Et Cie of Geneva, Switzerland) | 8 | 8 | 8 | 8 |
| -continued | | | | |
| Compound having the structure: 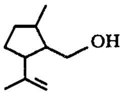 prepared according to Example I (bulked Fractions 3-11) | 6 | 0 | 0 | 0 |
| Compound having the structure: 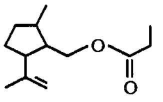 prepared according to Example II (bulked Fractions 3-13) | 0 | 6 | 0 | 0 |
| Compound having the structure: 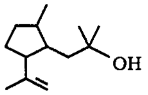 prepared according to Example III (bulked Fractions 5-10) or Example V | 0 | 0 | 6 | 0 |
| Compound having the structure: 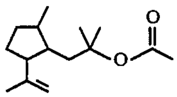 prepared according to Example IV (bulked Fractions 4-9) or Example VI (bulked Fractions 4-10) | 0 | 0 | 0 | 6 |

The compounds defined according to the generic structure:

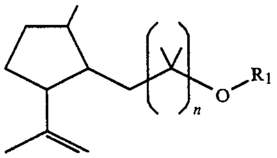

wherein $R_1$ represents hydrogen or $C_2$-$C_3$ acyl and n represents 0 or 1 impart, augment and enhance various aesthetically pleasing aroma nuances in the foregoing amber, woody formulation.

Each of the formulations, in each of the Examples VII(A), VII(B), VII(C) and VII(D) can be described as follows:

Example VII(A)—An amber, woody, cedarwood aroma with piney, camphoraceous, minty and rosy undertones and eucalyptus topnotes.

Example VII(B)—An amber, woody, cedarwood aroma with peppery, spicy, green and violet undertones and carnation and green topnotes.

Example VII(C)—An amber, woody cedarwood aroma with camphoraceous undertones and sweaty topnotes.

Example VII(D)—An amber, cedarwood, woody aroma with camphoraceous and vetiver undertones.

EXAMPLE VIII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| SUBSTANCE | AROMA DESCRIPTION |
|---|---|
| The compound having the structure: 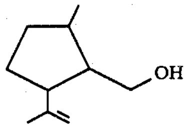 prepared according to Example I, bulked Fractions 3-11. | A piney, woody, camphoraceous, minty and rosy aroma with eucalyptus topnotes. |
| The compound having the structure: 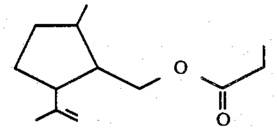 prepared according to Example II, bulked Fractions 3-13. | A woody, peppery, spicy, green and violet aroma with carnation, green and ambery topnotes. |
| The compound having the structure: 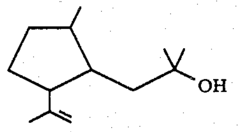 prepared according to Example III, (bulked Fractions 5-10) or Example V. | A woody, camphoraceous aroma with sweaty topnotes. |
| The compound having the structure: 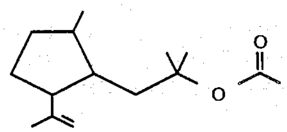 prepared according to Example IV (bulked Fractions 4-9) or Example VI, (bulked Fractions 4-10). | A woody, vetiver, ambery, camphoraceous aroma with cedarwood topnotes. |
| Perfume composition of Example VII (A) | An amber, woody, cedarwood aroma with piney, camphoraceous, minty and rosy undertones and eucalyptus topnotes. |
| Perfume composition of Example VII (B) | An amber, woody, cedarwood aroma with peppery, spicy, green and violet undertones and carnation and green topnotes. |
| Perfume composition of Example VII (C) | An amber, woody, cedarwood aroma with camphoraceous undertones and sweaty topnotes. |
| Perfume composition of Example VII (D) | An amber, cedarwood, woody aroma with camphoraceous and vetiver undertones. |

EXAMPLE IX

PREPARATION OF COLOGNES AND HANDKERCHIEF PERFUMES

Compositions as set forth in Table II of Example VIII are incorporated into colognes at concentrations of 2.0%, 2.5%, 3.0%, 3.5%, 4.0%, 4.5%, and 5.0% in 80%, 85%, 90% and 95% acqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VIII are imparted to the colognes and to the handkerchief perfumes at all levels indicated.

EXAMPLE X

PREPARATION OF SOAP COMPOSITIONS

One hundred grams of soap chips (per sample) (IVORY ® produced by the Procter & Gamble Company of Cincinnati, Ohio), are each mixed with one gram samples of substances as set forth in Table II of Example VIII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VIII.

EXAMPLE XI

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VIII. Each of the detergent samples has an excellent aroma as indicated in Table II of Example VIII.

EXAMPLE XII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table II of Example VIII.

Fabric softening compositions prepared according to Example I at column 15 of U.S. Pat. No. 3,632,396 having aroma characteristics as set forth in Table II of Example VIII supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VIII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example VIII, supra.

EXAMPLE XIII

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example VIII | 0.10 weight percent |

The perfuming substances as set forth in the Table II of Example VIII add aroma characteristics as set forth in Table II of Example VIII which are rather intense and aesthetically pleasing to the users of the soft-feel, good-hold pump hair sprays.

EXAMPLE XIV

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example VIII is added to the mixture. The resulting mixture is cooled to 40° C. and blending is carried out for an additional one hour in each case. At the end of this blending period, the resulting material has a pleasant fragrance as indicated in Table II of Example VIII.

EXAMPLE XV

IMPREGNATED PLASTICS AND AIR FRESHENER

Scented polyethylene pellets having pronounced aromas as set forth in Table II of Example VIII are prepared as follows:

Seventy-five pounds of polyethylene having a melting point of about 220° F. is heated to about 230° F. in a container of the kind illustrated in FIGS. 7 and 8. 12.5 Pounds of one of the perfumery substances set forth in Table II of Example VIII, supra is then quickly added to the liquified polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the perfumery substance of Table II of Example VIII through the orifices 234 (whereby such material exits through the orifices 234). The liquid falling through the orifices 234 solidifies almost instanteously upon impact with the moving cooled conveyor 238. Polyethylene beads or pellets having pronounced aromas as set forth in Table II of Example VIII are thus formed. These pellets may be called "master pellets".

50 Pounds of the aroma bearing master pellets are then added to 1000 pounds of unscented polyethylene powder and the mass is heated to the liquid state. The liquid is molded into thin sheets or films. The thin sheets or films have pronounced aromas as set forth in Table II of Example VIII. The sheets or films are cut into strips 0.25" in width×3" in length and employed in standard air freshening apparatus.

EXAMPLE XVI

TREATED PLASTICS AND AIR FRESHENER

100 Pounds of polypropylene are heated to about 300° F. 15 Pounds of one of the perfumery substances of Table II of Example VIII are added to the liquified polypropylene. The procedure is carried out in the apparatus shown in FIGS. 7 and 8. After mixing for about eight minutes, the valve "V" is opened to allow exit of the polypropylene mixture containing the perfumery substance whereby solid pellets having pronounced aromas as set forth in Table II of Example VIII are formed on the conveyor. The pellets thus obtained are then admixed with about twenty times their weight of unscented polypropylene and the mixture is heated and molded into "spaghetti" tows. The spaghetti tows are cut into small cylinders approximately 0.1" in length×0.2" in diameter. The cylinders have strong and pleasant aromas as set forth in Table II of Example VIII.

The cylinders are used in standard air freshening apparatus to produce aesthetically pleasing aromas described according to Table II of Example VIII with no foul odors in environments surrounding the air freshening apparatus.

A portion of the cylinders are ground into small particles to be used in the deodorant stick of Example XVII, infra.

EXAMPLE XVII

DEODORANT STICK

A deodorant stick composition is prepared containing the following materials:

| Ingredients | Parts by Weight |
|---|---|
| Propylene Glycol | 65.00 |
| Sodium Stearate | 7.00 |
| Distilled Water | 23.75 |
| IRGASAN ® DP-300 (2,4,4-trichloro-2'-hydroxy diphenyl ether, manufactured by the Ciba-Geigy Chemical Co. and a Trademark of the Ciba-Geigy Chemical Co.) | 0.25 |
| Ground Polymer containing one of the fragrance materials of Table II of Example VIII prepared according to Example XVI, supra | 4.00 |

The ingredients are combined without the ground polymer and heated to 75° C. These ingredients are mixed and continue to be heated until the sodium stearate has dissolved. The resulting mixture is cooled to 40° C. and the ground fragrance-containing polymer (containing one of the perfume materials of Table II of Example VIII, supra) is added and mixed at 40° C. until a suspension is formed. The resulting suspension is placed into molds and the molds are cooled to 10° C. and then opened thereby yielding deodorant sticks which are useful in deodorizing and giving rise to aesthetically pleasing aromas as set forth in Table II of Example VIII.

What is claimed is:

1. A process for augmenting or enhancing the aroma of a consumable material selected from the group consisting of perfume compositions, colognes and perfumed articles comprising the step of adding to said consumable material, an aroma augmenting or enhancing quantity of at least one 2-isopropenyl-5-methylcyclopentanealkanols and esters thereof defined according to the structure:

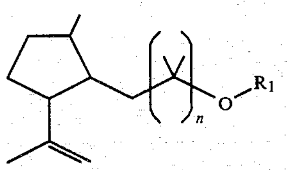

wherein $R_1$ represents hydrogen or $C_2$–$C_3$ acyl and n represents 0 or 1.

2. The process of claim 1 wherein the 2-isopropenyl-5-methylcyclopentanealkanols and esters thereof has the structure:

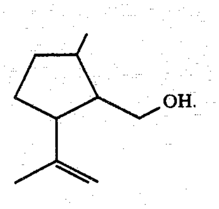

3. The process of claim 1 wherein the 2-isopropenyl-5-methylcyclopentanealkanols and esters thereof has the structure:

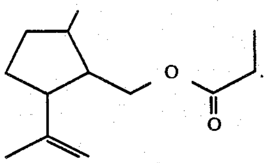

4. The process of claim 1 wherein the 2-ispropenyl-5-methylcyclopentanealkanols and esters thereof has the structure:

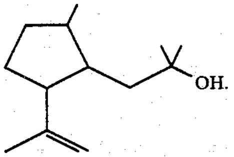

5. The process of claim 1 wherein the 2-isopropenyl-5-methyl-cyclopentanealkanols and esters thereof has the structure:

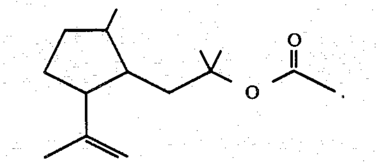

6. The process of claim 1 wherein the consumable material is a perfume composition, cologne or perfumed polymer.

7. The process of claim 1 wherein the consumable material is a perfumed article and the perfumed article is a solid or liquid anionic, cationic, nonionic or zwitterionic detergent.

8. The process of claim 1 wherein the consumable material is a perfumed article and the perfumed article is a fabric softener composition or fabric softener article.

9. An 2-isopropenyl-5-methylcyclopentanealkanol or ester thereof having the structure:

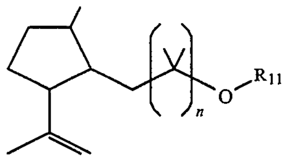

wherein n is 0 or 1 and $R_{11}$ represents $C_2$–$C_3$ acyl.

* * * * *